US010086005B2

(12) United States Patent
Finkelman et al.

(10) Patent No.: US 10,086,005 B2
(45) Date of Patent: Oct. 2, 2018

(54) METHODS FOR SUPPRESSING ALLERGIC REACTIONS

(71) Applicants: University of Cincinnati, Cincinnati, OH (US); U.S. Department of Veterans Affairs, Washington, DC (US); Children's Hospital Medical Center, Cincinnati, OH (US)

(72) Inventors: Fred D. Finkelman, Cincinnati, OH (US); Marat V. Khodoun, Mason, OH (US); Suzanne C. Morris, Mason, OH (US)

(*) Notice: Subject to any disclaimer, the term of this patent is extended or adjusted under 35 U.S.C. 154(b) by 0 days.

(21) Appl. No.: 15/836,095

(22) Filed: Dec. 8, 2017

(65) Prior Publication Data

US 2018/0092929 A1   Apr. 5, 2018

Related U.S. Application Data

(60) Continuation-in-part of application No. 15/704,097, filed on Sep. 14, 2017, which is a division of application No. 14/633,305, filed on Feb. 27, 2015, now Pat. No. 9,795,618, application No. 15/836,095, which is a continuation-in-part of application No. 14/111,208, filed as application No. PCT/US2012/033319 on Apr. 12, 2012, now Pat. No. 9,868,786.

(60) Provisional application No. 61/946,212, filed on Feb. 28, 2014, provisional application No. 61/474,566, filed on Apr. 12, 2011.

(51) Int. Cl.
| | |
|---|---|
| *A61K 39/395* | (2006.01) |
| *C07K 16/00* | (2006.01) |
| *C12P 21/08* | (2006.01) |
| *A61K 31/573* | (2006.01) |
| *A61K 45/06* | (2006.01) |
| *C07K 16/42* | (2006.01) |
| *A61K 31/335* | (2006.01) |
| *A61K 31/506* | (2006.01) |
| *A61K 31/137* | (2006.01) |
| *A61K 31/675* | (2006.01) |
| *A61K 31/4409* | (2006.01) |
| *A61K 31/4439* | (2006.01) |
| *A61K 39/00* | (2006.01) |

(52) U.S. Cl.
CPC .......... *A61K 31/573* (2013.01); *A61K 31/137* (2013.01); *A61K 31/335* (2013.01); *A61K 31/4409* (2013.01); *A61K 31/4439* (2013.01); *A61K 31/506* (2013.01); *A61K 31/675* (2013.01); *A61K 45/06* (2013.01); *C07K 16/4291* (2013.01); *A61K 2039/505* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,165,799 | A | 12/2000 | Kinet |
| 6,488,937 | B1 | 12/2002 | Smits |
| 7,384,633 | B2 | 6/2008 | Sugimura |
| 7,655,229 | B2 | 2/2010 | Chan |
| 7,662,926 | B2 | 2/2010 | Chan et al. |
| 7,879,334 | B1 | 2/2011 | Saxon et al. |
| 8,003,127 | B2 | 8/2011 | Leveridge et al. |
| 8,968,738 | B2 | 3/2015 | Mitre |
| 2005/0158303 | A1 | 7/2005 | Liu |
| 2005/0175638 | A1 | 8/2005 | Esch |
| 2009/0010924 | A1 | 1/2009 | Wu et al. |
| 2010/0158898 | A1 | 6/2010 | Liu et al. |
| 2013/0243750 | A1 | 9/2013 | Scheerens et al. |
| 2014/0314783 | A1 | 10/2014 | Finkelman et al. |

OTHER PUBLICATIONS

Meglio et al, "A Protocol for Oral Desensitization in children with IgE-mediated cow's milk allergy," European J. of Allergy and Clinical Immunology 59(9): 980-87 (2004).
Khodoun et al, "Rapid polyclonal desensitization with antibodies to IgE and FcεRLA," J. Allergy Clin. Immunol, pp. 1555-1564, Jun. 2013.
Khodoun et al, "Rapid desensitization of mice with anti-FcgRIIb/FcgRIII mAb safely prevents IgG-mediated anaphylaxis," J. Allergy Clin. Immunol. pp. 1375-1387, Dec. 2013.
Mirkina et al, "Inhibition of human cord blood-derived mast cell resposes by anti-FcεRI mAb 15/1 versus anti-IgE Omalizumab," Immunology Letters 109 (2007) pp. 120-128.
Gaestel et al, "Targeting innate immunity protein kinase signalling in inflammation," Nature.com, Jun. 2009, vol. 8, pp. 480-499.
Bakema et al, The human immunoglobulin A Fc receptor F calphaRI:a multifaceted regulator of mucosal immunity; Mucosal immunity 4(6): 612-624, 2011.
Tang et al, Epidemiology of Anaphysiaxis, Curr. Opin Allergy Clin Immunol Aug. 2009, 9(4): 351-6.
Decker, WW et al, The etiology and incidence of anaphlaxis in Rochester, Minnesota; a report from the Rochester Epidemiology Project. J. Allergy Clin Immunol 2008, 122:1161-1165.
Liew et al, Anaphylaxis Fatalities and Admissions in Australia; J Allergy Clin Immunol 2008; 123: 434-442.
Rafi et al, Effects of omalizumab in patients with food allergy; Allergy Asthma Proc. Jan. 2010; 31(1): 76-83.
Hansel et al, The safe and side effects of monoclonal antibodies; Nat Rev Drug Discov. Apr. 2010; 9(4): 325-338, ePub Mar. 22, 2010.

(Continued)

*Primary Examiner* — Nora M Rooney
(74) *Attorney, Agent, or Firm* — Dinsmore & Shohl LLP (57) ABSTRACT

A method of treating a subject suffering from an allergic disorder is provided, the method including inducing rapid desensitization to an allergen, the rapid desensitization effectuated by: administering to the subject a plurality of equal doses of a first anti-FcεRIα monoclonal antibody, wherein the plurality of equal doses are administered over a 6 to 8 hour period and wherein each dose is lower than a level required to induce shock, thereby inducing rapid desensitization to the allergen. Monoclonal antibodies and methods of co-administering or consecutively administering a combination thereof to effectuate rapid desensitization are also provided.

20 Claims, 7 Drawing Sheets

Specification includes a Sequence Listing.

(56) References Cited

OTHER PUBLICATIONS

Mulla et al, Anaphylaxis in Olmsted County: Seasonal pattern and suggestions for epidemiologic analysis; Letter to be Editor; J Allergy Clin Immunol May 2009, p. 1194.

SEQUENCE LISTING

```
<160> NUMBER OF SEQ ID NOS: 4

<210> SEQ ID NO 1
<211> LENGTH: 360
<212> TYPE: DNA
<213> ORGANISM: Mus musculus
<220> FEATURE:
<221> NAME/KEY: misc_feature
<223> OTHER INFORMATION: IB10 heavy chain variable region

<400> SEQUENCE: 1
caggtccaac tgcagcagcc tggggctgag ttggtgaggc ctggagcttc agtgaagctg      60
tcctgcaagg cttctggcta ctccttcacc agctactgga tgaactgggt gaaccagagg     120
cctggacaag gccttgagtg gattggcatg attcatcctt ccgatagtga aactaggtta     180
aatccgaact tcaaggacag ggccacattg actgtagaca aatcttccag cacagcctac     240
atgcaactca gcagcccgac atctgaggac tctgcggtct attactgtgc aagagggagt     300
ctatatgatg gttacctgtt tctttactgg ggccaaggga ctctggtcac tgtctctgca     360

<210> SEQ ID NO 2
<211> LENGTH: 339
<212> TYPE: DNA
<213> ORGANISM: Mus musculus
<220> FEATURE:
<221> NAME/KEY: misc_feature
<223> OTHER INFORMATION: IB10 light chain variable region

<400> SEQUENCE: 2
gatattgtga tgacccaatc tccactctcc ctacctgtca gtcttggaga tcaggcctcc      60
atctcttgca gatctagtca gagcattcta catagtaatg gagacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc atatgttcca     300
ttcacgttcg gctcggggac aaagttggaa ataaaacgg                            339
```

```
<210> SEQ ID NO 3
<211> LENGTH: 351
<212> TYPE: DNA
<213> ORGANISM: Mus musculus
<220> FEATURE:
<221> NAME/KEY: misc_feature
<223> OTHER INFORMATION: IE7 heavy chain variable region

<400> SEQUENCE: 3
caggtgcagc tgcaggagtc aggggggagac gtagtgaagc tggagggtc cctgaaactc         60 tcctgtgcag cctctggatt cactttcagt ttctatggca tgtcttgggt tcgtcagact        120
ccagacaaga aactggagtg ggtcgcaacc attagtggtg gtggtaatta cacctactat        180
ccagacagtg tgaaggggcg attcaccatc tccagagaca atgccatgaa caccctttac        240
ctgcaaatga acagtctgaa gtctgaagac acagccatgt attattgtgt gagagcctac        300
tatggtaatt ggaattctta ctggggccaa gggactctgg tcactgtctc t                351

<210> SEQ ID NO 4
<211> LENGTH: 324
<212> TYPE: DNA
<213> ORGANISM: Mus musculus
<220> FEATURE:
<221> NAME/KEY: misc_feature
<223> OTHER INFORMATION: IE7 light chain variable region

<400> SEQUENCE: 4
gatatcgtga tgacccaaac tccatcttcc atgtatgcat ctctaggaga gagagtcact         60
atcacttgca aggcgagtca ggacattaat aactatttaa gctggttcca gcagaaacca        120
gggagatctc ctaagaccct gatctatcgt gcaaacagat tgatggatgg ggtcccatca        180
aggatcagag gcagtggatc tgggcaagat tattctctca ccatcagcag cctggagtat        240
gaagatatgg gaatttatta ttgtctacta tataatgagt ttccgtggat gttcggtgga        300
ggcaccaagc tggaaatcaa acgg                                               324
```

METHODS FOR SUPPRESSING ALLERGIC REACTIONS

RELATED APPLICATIONS

This application is a continuation-in-part of U.S. application Ser. No. 14/111,208, filed Feb. 25, 2014, which is a § 371 National Stage Entry of PCT/US2012/033319, filed Apr. 12, 2012, and claims benefit under 35 U.S.C. § 119(e) to U.S. Provisional Application Ser. No. 61/474,566, filed Apr. 12, 2011; and is also a continuation-in-part of U.S. application Ser. No. 15/704,097, filed Sep. 14, 2017, which is a divisional of U.S. application Ser. No. 14/633,305, filed Feb. 27, 2015, now U.S. Pat. No. 9,795,618, issued Oct. 4, 2017, and claims the benefit under 35 U.S.C. § 119(e) to U.S. Provisional Application Ser. No. 61/946,212, filed Feb. 28, 2014, the entire disclosures of which are incorporated herein by this reference.

FEDERALLY SPONSORED RESEARCH OR DEVELOPMENT

This invention was made with Government support under R01 AI113162-02 awarded by the National Institute of Health. The Government has certain rights in the invention.

TECHNICAL FIELD

The subject matter of this application relates to methods for suppressing IgE- and IgG-mediated allergic reactions through monoclonal antibody (mAb) applications. More specifically, methods are herein provided for safe induction of rapid desensitization to an allergen via repeated equal low doses of anti-FcεRIα mAbs.

BACKGROUND

Allergic disorders, including allergic rhinitis, asthma, atopic dermatitis, food allergy, and anaphylaxis are an increasingly common cause of morbidity in developed countries and, in the case of asthma and anaphylaxis, a not infrequent cause of death. All of these disorders are mediated, to some extent, by immediate hypersensitivity reactions in which the activation of inflammatory cells by the crosslinking of immunoglobulin (Ig) Fc receptors (R) leads rapidly to the release of vasoactive mediators, such as histamine and platelet activating factor (PAF), cytokines, and proteolytic enzymes. Such immediate hypersensitivity reactions are the critical pathogenic mechanism in anaphylaxis and IgE-mediated food allergy and an important contributing mechanism in asthma, atopic dermatitis, and allergic rhinitis. In both humans and mice, immediate hypersensitivity reactions can be mediated by antigen cross-linking of antigen-specific IgE bound to the high affinity IgE receptor, FcεRI, on mast cells and basophils, while the crosslinking of FcγRIII or FcγRIV on macrophages, neutrophils, and/or basophils by IgG/antigen complexes can mediate immediate hypersensitivity in mice and possibly also in humans.

Although some of these allergic disorders can be treated pharmacologically, manipulation of the immune system by administering increasing doses of allergen over time can also be an efficacious, albeit sometimes risky, way to suppress disease. Two different general strategies of allergen immunotherapy have been widely used. Standard immune desensitization involves administration of increasing doses of allergen through a subcutaneous, oral, rectal, or sublingual route over a period of weeks to months. This procedure suppresses IgE-mediated disease through at least two mechanisms: 1) increased production of IgG antibodies that can activate an inhibitory Ig receptor, FcγRIIb, and intercept antigen before it can access mast cell and basophil IgE; and 2) induction of regulatory T cells that can suppress production of IgE. Rapid desensitization procedures, in contrast, administer increasing concentrations of allergen over a period of hours or days. This time period is too short to work by altering Ig production; however, the precise mechanisms are not established. Unlike conventional desensitization, the suppressive effects of rapid desensitization can be quickly lost when allergen administration is discontinued.

To date, rapid desensitization techniques have involved the administration of allergen. Although effective, this can be of limited utility in individuals who are allergic to multiple antigens. In addition, the presence of serum antibodies, including IgG, which can bind inoculated allergens, may make rapid desensitization more risky if the initial, small allergen doses are neutralized before they can access mast cell or basophil bound IgE, so that the first dose of allergen that interacts with cell-bound IgE is sufficiently large to induce a severe reaction.

It was previously shown that although administration of a single large dose of the anti-FcεRIα mAb, MAR-1, the anti-IgE mAb, EM-95, or the anti-FcγRIIb/RIII mAb, 2.4G2, can induce an anaphylactic response, administration of sequentially increasing doses of any of these mAbs, starting with a dose too small to induce detectable disease, as in rapid desensitization with allergen, inhibits IgE- or IgG-mediated immediate hypersensitivity. The results of these studies in a mouse model demonstrated the feasibility of this approach.

It has now been found that repeated equal doses of one or more anti-FcεRIα mAbs, each administered at a level lower than that required to induce shock, can be administered to effectuate rapid desensitization to an allergen.

These and additional objects, embodiments, and aspects of the invention will become apparent by reference to the Figures and Detailed Description below.

SUMMARY

Accordingly, the instant disclosure provides methods and antibodies for inducing rapid desensitization to an allergen. In one embodiment, a method of treating a subject suffering from an allergic disorder is provided, the method comprising inducing rapid desensitization to an allergen, said rapid desensitization effectuated by: administering to the subject a plurality of equal doses of a first anti-FcεRIα monoclonal antibody, wherein the plurality of equal doses are administered over a 6 to 8 hour period and wherein each dose is lower than a level required to induce shock, thereby inducing rapid desensitization to the allergen.

In another embodiment, a monoclonal antibody that specifically binds human or rhesus monkey FcεRIα is provided, wherein said antibody is IE7 and comprises a heavy chain variable region comprising SEQ ID NO: 3 and a light chain variable region comprising SEQ ID NO: 4.

In another embodiment, a monoclonal antibody that specifically binds human or rhesus monkey FcεRIα that is not IgE-associated is provided, wherein said antibody is IB10 and comprises a heavy chain variable region comprising SEQ ID NO: 1 and a light chain variable region comprising SEQ ID NO: 2.

All references (e.g., printed publications such as books, papers, patents, patent applications, catalogs, databases) are incorporated herein by reference. In the event of a conflict or inconsistency, the present specification, as modified by any amendments thereto, shall control.

These and other embodiments will be more clearly understood by reference to the detailed disclosure and accompanying figures.

BRIEF DESCRIPTION OF THE FIGURES

The embodiments set forth in the figures are illustrative and exemplary in nature and not intended to limit the subject matter defined by the claims. The following detailed description of the illustrative embodiments can be understood when read in conjunction with the following drawings, wherein:

DETAILED DESCRIPTION

Unless otherwise defined, all technical and scientific terms used herein have the same meaning as commonly understood by one of ordinary skill in the art to which this invention pertains. The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "and combinations thereof" means a combination including at least one of the foregoing elements.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Wild, D., The Immunoassay Handbook, 3rd Ed., Elsevier Science, 2005; Gosling, J. P., Immunoassays: A Practical Approach, Practical Approach Series, Oxford University Press, 2005; Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; J. D. Pound (Ed.) Immunochemical Protocols, Methods in Molecular Biology, Humana Press; 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975); the contents of each of which are incorporated herein by reference.

As used herein, the term "rapid desensitization" refers to rapid desensitization to an allergen; rapid desensitization in the presently disclosed embodiments is accomplished by administering repeated equal concentrations of one or more anti-FcεRIα monoclonal antibodies over a period of hours. The administration in certain embodiments can be from two to eight administrations or more over a period of one to 24 hours. The doses can be provided at intervals such as 30 minutes, 60 minutes, 90 minutes, or more (or a combination of the times). Rapid desensitization is contrasted with standard immune desensitization that involves administration of increasing doses of allergen through a subcutaneous, oral, rectal or sublingual route over a period of weeks to months.

As used herein, the term "equal doses" refers to two or more doses of an anti-FcεRIα monoclonal antibody, such as doses provided in methods of inducing rapid desensitization, wherein each subsequent dose is the same as, or equal to, the first dose of the anti-FcεRIα monoclonal antibody. Each dose administered in the methods of the present disclosure is lower than a level required to induce shock.

As used herein, the term "shock" can refer to a clinical diagnosis or standard or can refer to signs of shock such as a change in a subject's temperature following an administration of immunoglobulin or during the course or desensitization. Other factors could include changes in circulatory function, pallor, sweating, weak pulse, and very low blood pressure.

As used herein, the term "allergen" refers to a substance that produces an immune response; such responses can include hypersensitivities and allergies. The allergen can, for example, be a protein, can be from food (such as peanut butter or strawberries) or can be from the environmental surroundings. Allergens may be naturally occurring or of synthetic origin and include among other things pollen, mold spores, dust, animal dander, insect debris, foods, blood serum, and drugs (including cosmetics). In certain embodiments, a food allergen is selected from the group consisting of peanut, tree nut, and dairy.

As used herein, the term "administering" refers to introducing a substance to a subject; this can be through, among other ways, known clinical techniques; non-limiting examples include intravenously, orally, subcutaneously, intraperitoneally, or intramuscularly; and can be in known clinical forms; non-limiting examples include pills, inhalants or injectables (among others).

Unless otherwise indicated, all numbers expressing quantities used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Anaphylaxis is the most severe form of allergic reaction and, if untreated, can result in death. Around 1% of allergic reactions are severe (Tang M L, et al., *Epidemiology of anaphylaxis*, Curr. Opin. Allergy Clin. Immunol. 9(4):351-56 (August 2009)). Prevalence of anaphylaxis is relatively high in the United States as compared to other developed countries (per 100,000 person-years: USA—49.8; Australia—13; UK—8.4) and has more than doubled in the last two decades. Rates of death from drug induced anaphylaxis have risen in some countries by 300% over the last decade. (Decker W W, et al., *The etiology and incidence of anaphylaxis in Rochester, Minn.: a report from the Rochester Epidemiology Project*, J. Allergy Clin. Immunol. 122:1161-65 (2008); Liew W K, et al., *Anaphylaxis fatalities and admissions in Australia*, J. Allergy Clin. Immunol. 123:434-42 (2008)). Many cases of the food-, insect-, and drug-related cases of anaphylaxis are associated with elevated IgE level. (Rafi A, et al., *Effects of omalizumab in patients with food allergy*, Allergy Asthma Proc. 31(1):76-83 (January 2010).

It has now been discovered that peritoneal mast cells in huFcεRIα mice can be safely and effectively desensitized with 6 to 8 hourly low doses of anti-huFcεRIα mAb.

Methods of Rapid Desensitization

In one embodiment, a method of treating a subject suffering from an allergic disorder is provided, the method comprising inducing rapid desensitization to an allergen, said rapid desensitization effectuated by: administering to the subject a plurality of equal doses of a first anti-FcεRIα monoclonal antibody, wherein the plurality of equal doses are administered over a 6 to 8 hour period and wherein each dose is lower than a level required to induce shock, thereby inducing rapid desensitization to the allergen. In certain embodiments, a dose of anti-FcεRIα monoclonal antibody is administered hourly. In a specific embodiment, 6 to 8 equal hourly doses of a first anti-FcεRIα monoclonal are administered, wherein each dose is lower than a level required to induce shock, thereby inducing rapid desensitization to the allergen.

Each dose of the anti-FcεRIα monoclonal antibodies of the present methods is lower than a level required to induce shock in the subject. In a specific embodiment, the dose is about ½ the level required to induce shock in the subject. In another specific embodiment, the dose is less than about ½ the level required to induce shock in the subject, for example, the dose may be about ⅓, ¼, ⅕, ⅙, 1/7, ⅛, 1/10, or 1/16 the level required to induce shock in the subject, and the like. In certain embodiments, the dose for human subjects is from about 1 μg/hour to about 400 mg/hour. In a more specific embodiment, the dose for human subjects is from about 100 mg/hour to about 400 mg/hour.

Various anti-FcεRIα monoclonal antibodies are suitable for use in the presently disclosed methods. In certain embodiments, the anti-FcεRIα monoclonal antibody is an antibody that binds to all human and/or rhesus monkey FcεRIα. In a specific embodiment, the anti-FcεRIα monoclonal antibody is 1E7. 1E7 is a mouse IgG1 mAb that does not compete with IgE for binding to FcεRIα. 1E7 does not prevent IgE binding to human FcεRIα in vitro. 1E7 comprises the heavy chain variable region comprising SEQ ID NO: 3 and the light chain variable region comprising SEQ ID NO: 4. A biological material deposit of the 1E7 hybridoma (ATCC® Patent Deposit Designation PTA-125115) was made on Jun. 29, 2018 with the American Type Culture Collection (ATCC®), P.O. Box 1549, Manassas, VA., 20108, USA.

In another embodiment, the anti-FcεRIα monoclonal antibody only binds to FcεRIα that is not associated with IgE. In a specific embodiment, the anti-FcεRIα monoclonal antibody is 1B10. 1B10 competes with IgE for binding to FcεRIα. 1B10 prevents IgE binding to human FcεRIα in vitro. 1B10 comprises the heavy chain variable region comprising SEQ ID NO: 1 and the light chain variable region comprising SEQ ID NO: 2. A biological material deposit of the 1B10 hybridoma (ATCC® Patent Deposit Designation PTA-125116) was made on Jun. 29, 2018 with the American Type Culture Collection (ATCC®), P.O. Box 1549, Manassas, VA., 20108, USA.

In another embodiment, two or more anti-FcεRIα monoclonal antibodies are co-administered to the subject. In certain embodiments, a first anti-FcεRIα monoclonal antibody is administered alone for a plurality of doses (e.g. 3 to 4 doses), and then the first anti-FcεRIα monoclonal antibody and a second anti-FcεRIα monoclonal antibody are co-administered together for a plurality of doses (e.g., the last 3 to 4 doses). For example, in certain embodiments, a total of 6 to 8 equal hourly doses of the first anti-FcεRIα monoclonal antibody are administered, wherein each of the last 3 to 4 hourly equal doses of the first anti-FcεRIα monoclonal antibody is co-administered with a dose of the second anti-FcεRIα monoclonal antibody.

In another embodiment, a first anti-FcεRIα monoclonal antibody is administered for a plurality of doses (e.g. 2 to 8 doses), and then a second anti-FcεRIα monoclonal antibody is administered (e.g. 1 to 8 doses). For example, in certain embodiments 2, 3, 4, 5, 6, 7, or 8 equal doses of the first anti-FcεRIα monoclonal antibody are administered, followed by 1, 2, 3, 4, 5, 6, 7, or 8 equal doses of the second anti-FcεRIα monoclonal antibody. In certain embodiments, IE7 is the first anti-FcεRIα monoclonal antibody and IB10 is the second anti-FcεRIα monoclonal antibody.

When two or more monoclonal antibodies are co-administered, i.e., administered together, or consecutively administered, each dose of each monoclonal antibody is lower than a level required to induce shock. In certain embodiments, the doses of the first and second monoclonal antibodies are substantially the same, i.e., equal doses. In certain embodiments, each of the doses of the second monoclonal antibody is the same, i.e., an equal dose of the second monoclonal antibody.

In some embodiment, the first and second anti-FcεRIα monoclonal antibodies each bind to a different epitope of human and/or rhesus monkey FcεRIα. In certain embodiments, the first anti-FcεRIα monoclonal antibody is IE7 and the second anti-FcεRIα monoclonal antibody is IB10. In other embodiments, the first anti-FcεRIα monoclonal antibody is IB10 and the second anti-FcεRIα monoclonal antibody is IE7.

The following Examples are set forth to illustrate particular embodiments of the invention and should not be construed as limiting the full scope of the invention as defined by the claims and understood by a person of skill in the art.

EXAMPLES

Example 1

Figure 1:
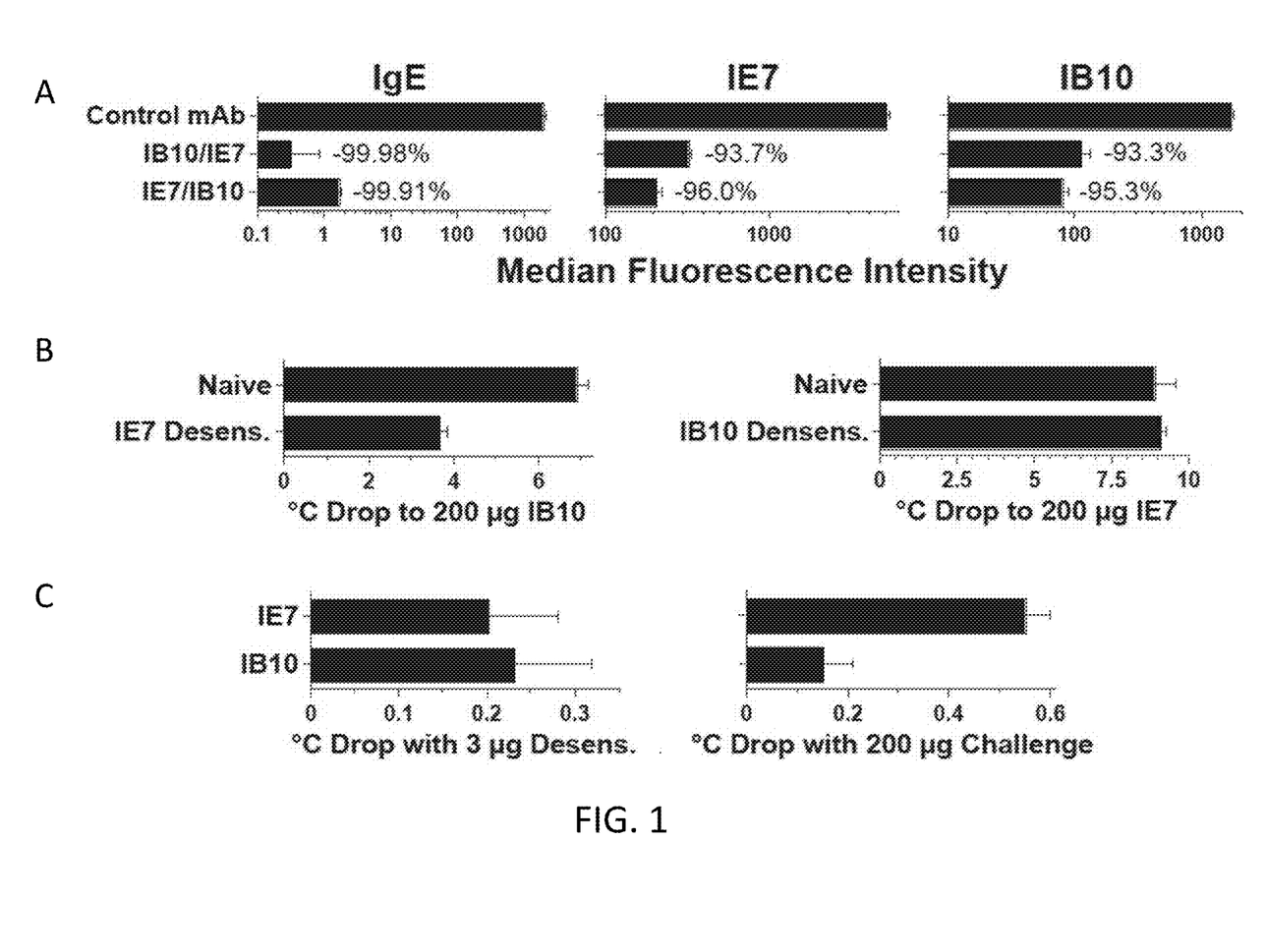
FIG. 1. (A) shows flow cytometry results for mouse peritoneal mast cells stained with fluorochrome-labeled anti-mouse IgE mAB (left panel), IE7 (center panel), or IB10 (right panel); (B) shows temperature change for huFcεRIα mice desensitized with IE7 and challenged with 200 μg IB10 (left panel); and desensitized with IB10 and challenged with 200 μg IE7 (right panel). (C) shows temperature change for huFcεRIα mice sensitized with mouse IgE mAB, desensitized with hourly 3 μg doses of control mAb (not shown), IB10 or IE7 (left panel), then challenged with 200 μg of the same mAb (right panel).

FIG. 1(C) shows temperature drop for huFcεRIα mice sensitized with mouse IgE mAB, then desensitized with hourly 3 μg doses of control mAb (not shown), IB10 or IE7 (left panel), then challenged with 200 μg of the same mAb (right panel). FIG. 1(B) shows temperature drop for huFcεRIα mice challenged with 200 μg of the other anti-FcεRIα mAb 18 hr after desensitization. Left panel shows results for mice desensitized with IE7 and then challenged with IB10. Right panel shows results for mice desensitized with IB10 and then challenged with IE7. FIG. 1(A) shows flow cytometry median fluorescence intensity for peritoneal mast cells from these mice stained with fluorochrome-labeled anti-mouse IgE mAB (left panel), IE7 (center panel), or IB10 (right panel). Results show treatment with low dose (i.e., lower than a level required to induce shock) anti-FcεRIα mAb desensitizes mouse mast cells in vivo.

Example 2

Figure 2:
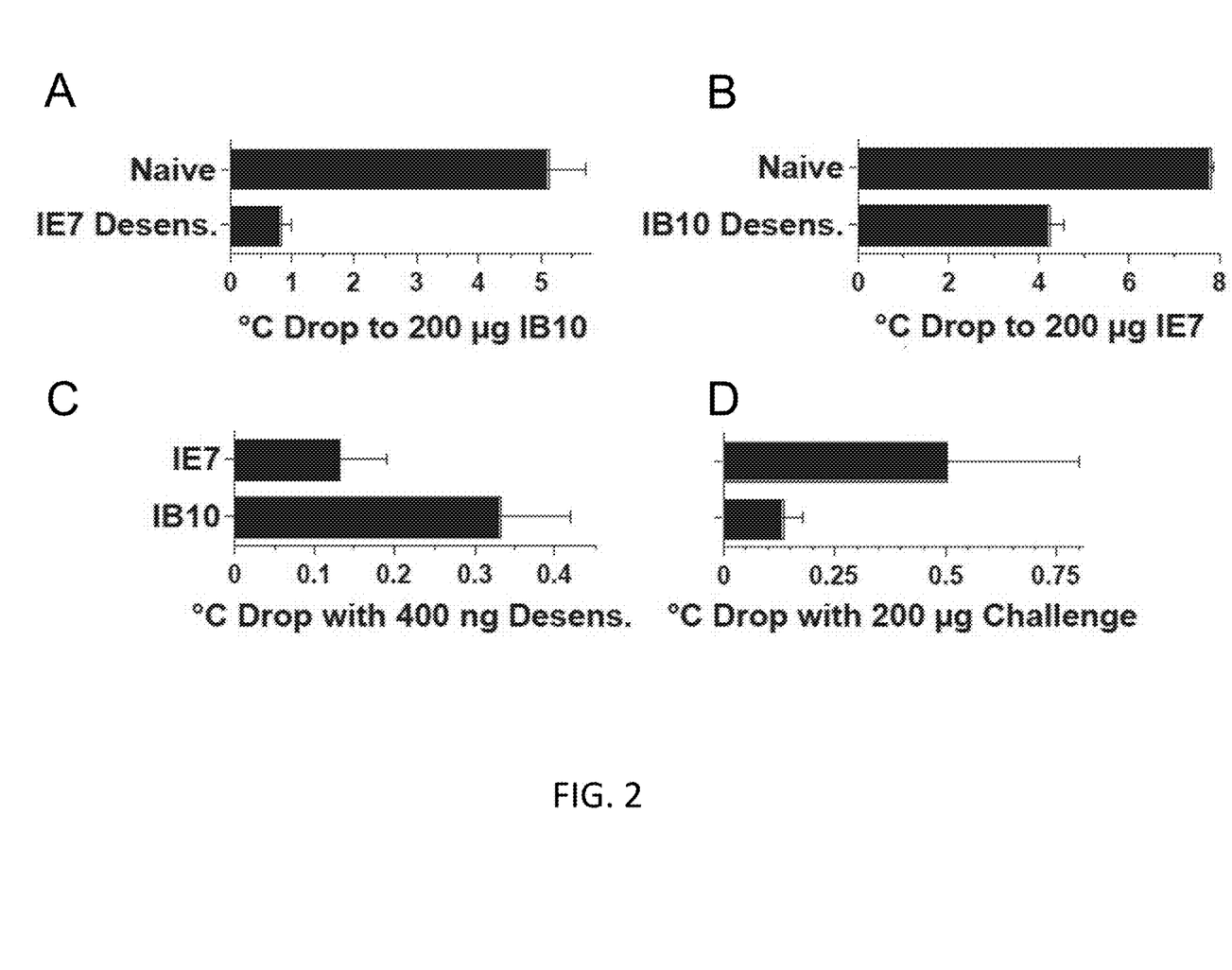
FIG. 2. (C) shows temperature change for huFcεRIα mice desensitized with seven repeated, hourly 400 ng i.p. doses of IE7 or IB10. (D) shows temperature change for mice challenged one hr later i.p. with 200 μg of the same mAb. (A) shows temperature change for naïve and IE7-desensitized mice challenged two hours after (D) intravenously (i.v.) with 200 μg of IB10. (B) shows temperature change for IB10-desensitized mice challenged two hours after (D) i.v. with 200 μg of IE7.

FIG. 2(C) shows temperature change for huFcεRIα mice desensitized with seven repeated, hourly 400 ng i.p. doses of IE7 or IB10. FIG. 2(D) shows temperature change (° C.) for these mice challenged one hr later i.p. with 200 μg of the same mAb. FIG. 2(A) shows temperature change for naïve and IE7-desensitized mice challenged two hours after (D), intravenously with 200 μg of IB10. FIG. 2(B) shows temperature change for IB10-desensitized mice challenged two hours after (D) i.v. with 200 μg of IE7. Results show IE7 is better than IB10 for initial small dose rapid desensitization.

Example 3

Figure 3:
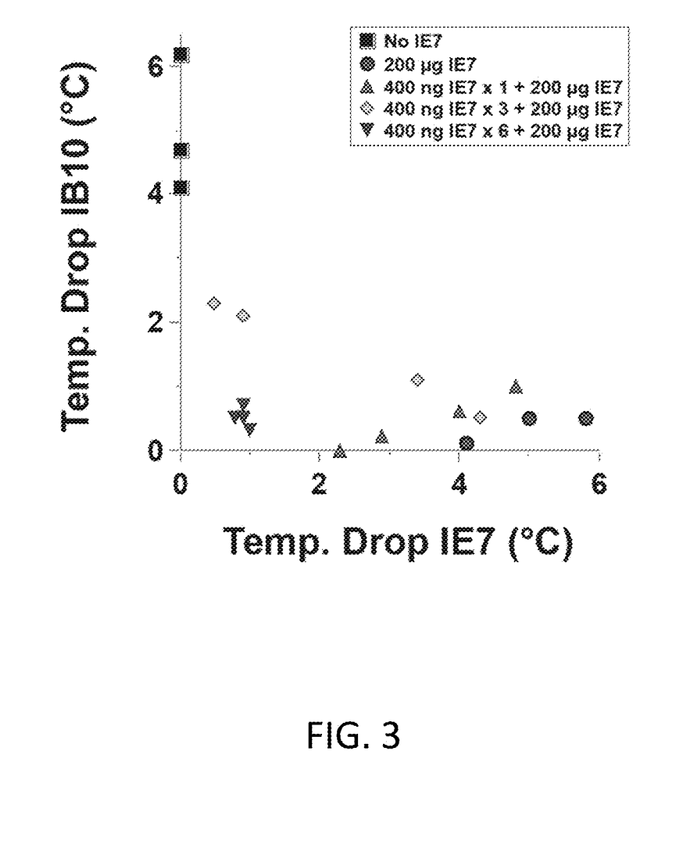
FIG. 3. Temperature change is shown for huFcεRIα mice injected i.p. every hour with IE7, followed one hour later with a 200 μg i.p. dose of IE7 and 2 hours after that with a 200 μg i.v. dose of IB10. Temperature drops shown are to the 200 μg doses of each mAb.

As shown in FIG. 3, huFcεRIα mice (4/group) were injected i.p. every hour with IE7 according to the figure legend (No IE7; 200 μg IE7; 400 ng IE7 (one dose); 400 ng IE7 (3 doses); 400 ng IE7 (six doses)), followed one hour later with a 200 μg i.p. dose of IE7 and 2 hours after that with a 200 μg i.v. dose of IB10. Temperature drops shown are to the 200 μg doses of each mAb. Results show seven repeated small doses of IE7 are sufficient to desensitize mast cells.

Example 4

Figure 4:
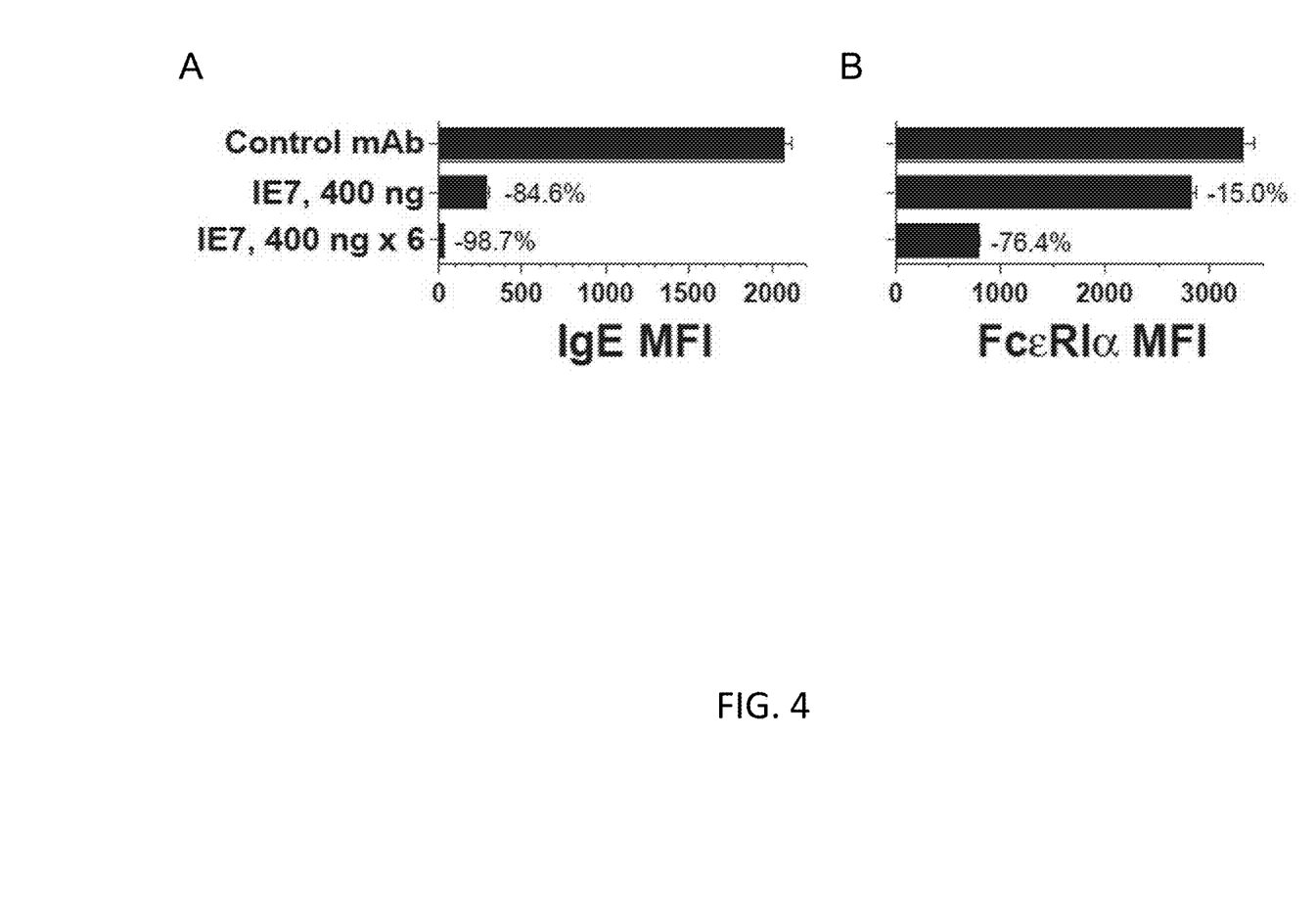
FIG. 4. Flow cytometry results for mouse peritoneal mast cells stained with fluorochrome-labeled anti-mIgE mAb (A) and anti-FcεRIα mAb (B) after treatment of huFcεRIα mice with IE7 or control.

As shown in FIG. 4, huFcεRIα mice were sensitized with mIgE, then injected i.p. with a control mAb, with a single 400 ng dose of IE7, or with 6 hourly 400 ng doses of IE7. One hour later, peritoneal mast cells from these mice were stained with fluorochrome-labeled anti-mIgE mAb (FIG. 4(A)) and anti-FcεRIα mAb (FIG. 4(B)) and analyzed by flow cytometry. Results show six small hourly doses of IE7 remove >98% of IgE from peritoneal mast cells.

Example 5

Figure 5:
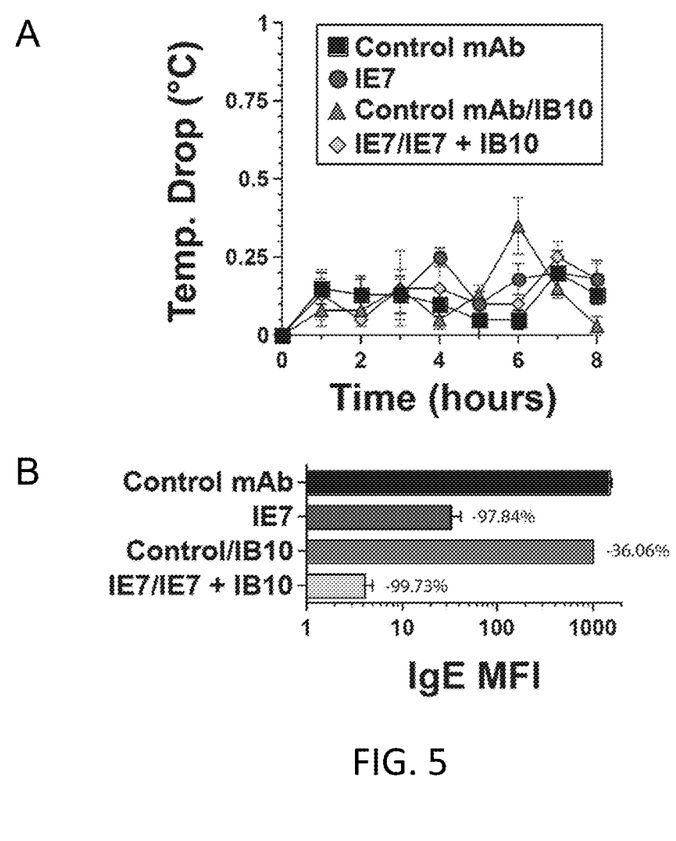
FIG. 5. (A) shows max temperature drop during the hour following each i.p. injection. (B) shows the amount of remaining IgE on peritoneal mast cells after desensitization, determined by immunofluorescence staining and flow cytometry.

As shown in FIG. 5, huFcεRIα mice (4/group) were first injected with 10 μg of mouse IgE anti-TNP mAb to load mast cells with IgE. Twelve hours later, different groups of mice were injected hourly i.p.: Group 1 for 8 hours with 400 ng/hour of an isotype control mouse IgG1 mAb; Group 2 with 400 ng/hour of IE7; Group 3 with 400 ng/hour of control mAb for 8 hours with 400 ng/hour of IB10 added during the last 4 hours; Group 4 with 400 ng/hour of IE7 for 8 hours with 400 ng/hour of IB10 added during the last 4 hours. FIG. 5(A) shows the maximum temperature drop during the hour following each i.p. injection. FIG. 5(B) shows the amount of remaining IgE on peritoneal mast cells after desensitization as determined by immunofluorescence staining and flow cytometry. Numbers to the right of bars indicate the mean percent of IgE that has been lost by mast cells from desensitized mice. Results show treatment with IB10 after rapid desensitization with small doses of IE7 removes most residual IgE from peritoneal mast cells.

Example 6

Figure 6:
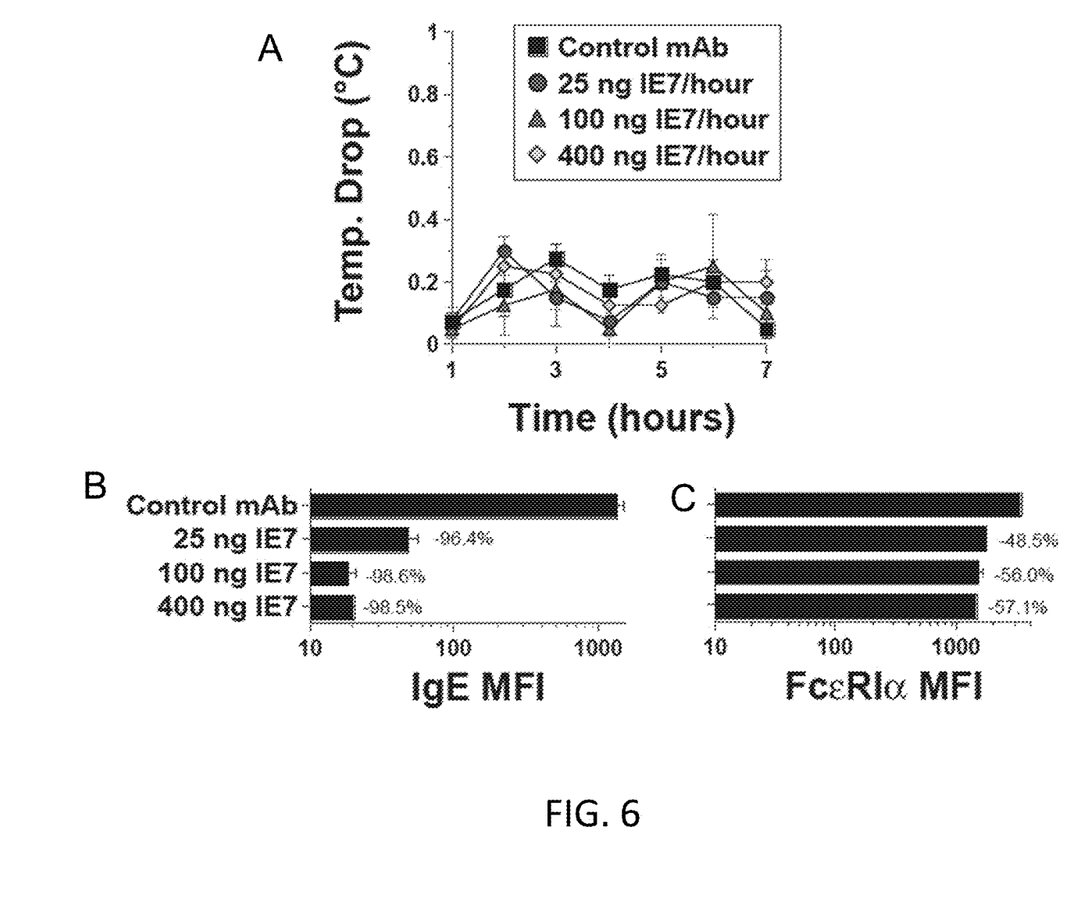
FIG. 6. (A) Temperature drop over time is shown for huFcεRIα mice sensitized with mouse IgE, then injected i.p. hourly for 7 hours with control mAb or IE7. One hour after the last dose, peritoneal mast cells were stained with fluorochrome-labeled anti-IgE mAb (B) and anti-FcεRIα mAb (C) and analyzed by flow cytometry.

As shown in FIG. 6, huFcεRIα mice were sensitized with mouse IgE, then next day mice were injected i.p. hourly for 7 hours with control mAb or the quantities of IE7 shown. Temperature drop over time is shown in FIG. 6(A). One hour after the last dose, peritoneal mast cells were stained with fluorochrome-labeled anti-IgE mAb FIG. 6(B) and anti-FcεRIα mAb FIG. 6(C) and analyzed by flow cytometry. Results show repeated 100 ng doses of IE7 remove >98% of IgE from peritoneal mast cells, but leave 40-50% of FcεRIα on these cells.

Example 7

Figure 7:
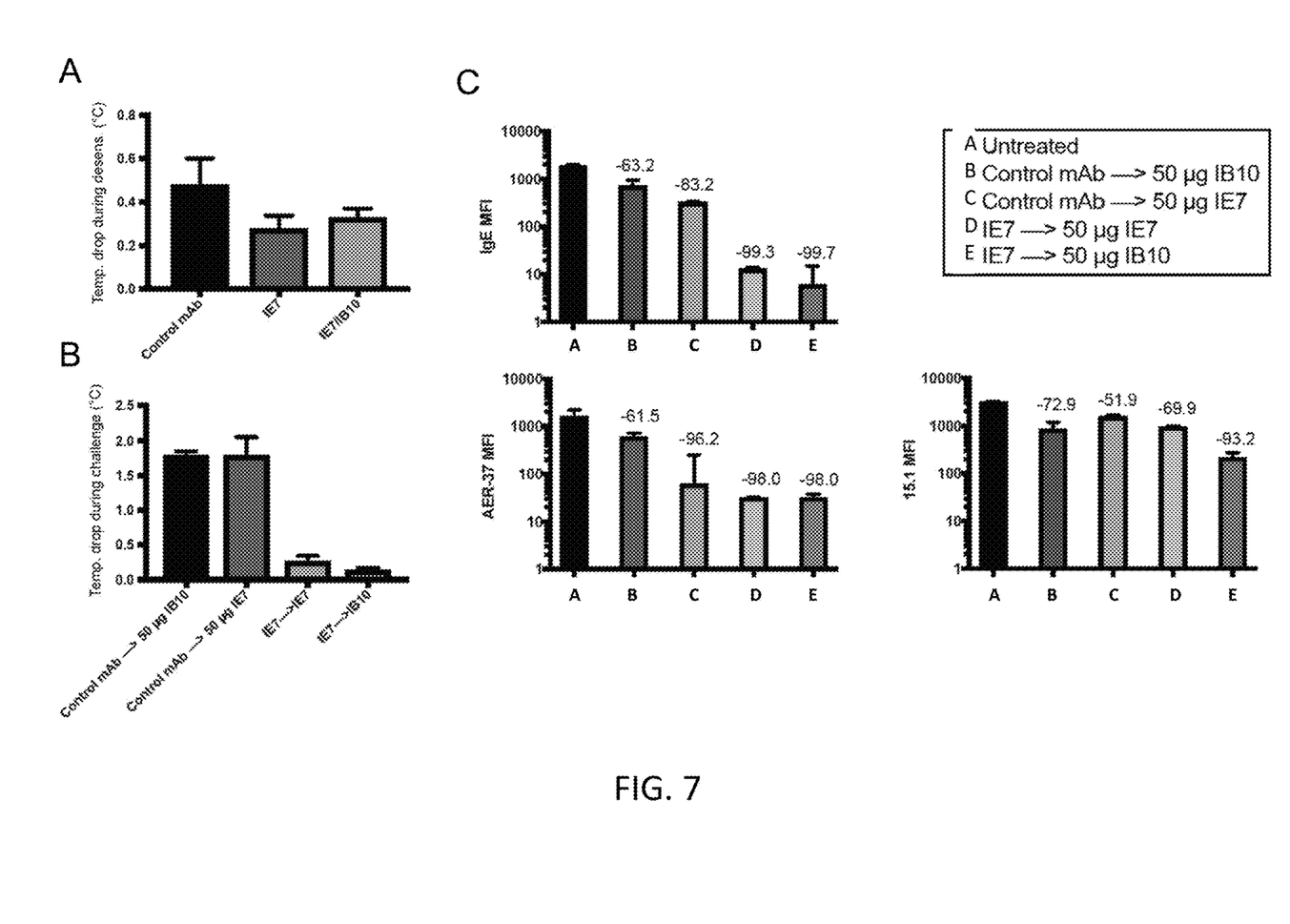
FIG. 7. (A) Temperature drop is shown for huFcεRIα mice sensitized with mouse IgE, then desensitized with 7 hourly i.p. injections of 400 μg of IE7 or mock-desensitized with control mAb. (B) Temperature drop is shown for mice challenged i.p. one hour later with 50 μg of IE7 or IB10. (C) Flow cytometry results for peritoneal mast cells from one hr post challenge stained with fluorochrome-labeled anti-mouse IgE (top panel), anti-FcεRIα mAb AER-37 (bottom left panel), or 15.1 (bottom right panel).

As shown in FIG. 7, huFcεRIα mice were sensitized with mouse IgE, then desensitized with 7 hourly i.p. injections of 400 μg of IE7 or mock-desensitized with control mAb.

Temperature drop is shown in FIG. 7(A). Mice were challenged i.p. one hour later with 50 μg of IE7 or IB10. Temperature drop is shown in FIG. 7(B). Peritoneal mast cells from these mice were obtained one hr post challenge and stained with fluorochrome-labeled anti-mouse IgE (FIG. 7(C), top panel), AER-37 (FIG. 7(C), bottom left panel), or 15.1 (FIG. 7(C), bottom right panel) and analyzed by flow cytometry. Results show rapid desensitization with repeated low doses of IE7, followed by IB10 is safe and removes >99% of IgE from peritoneal mast cells, which retain considerable FcεRIα.

Examples 1-7 show that peritoneal mast cells in huFcεRIα mice can be safely and effectively desensitized with 6-8 hourly 100-400 ng doses of anti-huFcεRIα mAb. It is noted that 400 ng is equal to about half the level required to cause shock in the mouse.

Examples 1-7 further show that a mAb that binds to all huFcεRIα (IE7) is more effective in methods of rapid desensitization than one that selectively binds to FcεRI that is not associated with IgE (IB10).

Examples 1-7 support the premise that serial treatment with a first anti-FcεRIα mAb followed by a second anti-FcεRIα mAb is more effective than either anti-FcεRIα mAb alone. Further, rapid desensitization of huFcεRIα mice with repeated small doses of IE7 or IE7 followed by IB10 is more effective at removing IgE than FcεRIα from peritoneal mast cells.

Various modifications of the present disclosure, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of flow cytometry analysis are similarly within the level of skill in the art.

Patents, publications, and applications mentioned in the specification are indicative of the levels of those skilled in the art to which the disclosure pertains. These patents, publications, and applications are incorporated herein by reference to the same extent as if each individual patent, publication, or application was specifically and individually incorporated herein by reference.

The foregoing description is illustrative of particular embodiments of the disclosure, but is not meant to be a limitation upon the practice thereof. The following claims, including all equivalents thereof, are intended to define the scope of the disclosure.

What is claimed:

1. A method of treating a subject suffering from an allergic disorder, the method comprising inducing rapid desensitization to an allergen, said rapid desensitization effectuated by: administering to the subject a plurality of equal doses of a first anti-FcεRIα monoclonal antibody, wherein the plurality of equal doses are administered over a 6 to 8 hour period and wherein each dose is lower than a level required to induce shock, thereby inducing rapid desensitization to the allergen.

2. The method of claim 1, wherein a dose of anti-FcεRIα monoclonal antibody is administered hourly.

3. The method of claim 1, wherein each dose is half the dose required to induce shock or less than half the dose required to induce shock.

4. The method of claim 1, wherein the first anti-FcεRIα monoclonal antibody is IE7, wherein IE7 comprises a heavy chain variable region comprising SEQ ID NO: 3 and a light chain variable region comprising SEQ ID NO: 4.

5. The method of claim 4, wherein the first anti-FcεRIα monoclonal antibody binds to human and rhesus monkey FcεRIα.

6. The method of claim 1, wherein the first anti-FcεRIα monoclonal antibody is IB10, wherein IB10 comprises a heavy chain variable region comprising SEQ ID NO: 1 and a light chain variable region comprising SEQ ID NO: 2.

7. The method of claim 6, wherein the first anti-FcεRIα monoclonal antibody only binds to FcεRIα that is not associated with IgE.

8. The method of claim 1, wherein the allergen is selected from the group consisting of protein, food, pollen, mold spores, dust, animal dander, insect debris, blood serum, drugs, cosmetics, and combinations thereof.

9. The method of claim 8, wherein the allergen is a food allergen selected from the group consisting of peanut, tree nut, and dairy.

10. The method of claim 1, further comprising subsequently administering a plurality of equal doses of a second anti-FcεRIα monoclonal antibody, wherein each dose is lower than a level required to induce shock, thereby inducing rapid desensitization to the allergen.

11. The method of claim 10, wherein the first anti-FcεRIα monoclonal antibody is IE7, wherein IE7 comprises a heavy chain variable region comprising SEQ ID NO: 3 and a light chain variable region comprising SEQ ID NO: 4, and the second anti-FcεRIα monoclonal antibody is IB10, wherein IB10 comprises a heavy chain variable region comprising SEQ ID NO: 1 and a light chain variable region comprising SEQ ID NO: 2.

12. The method of claim 1 comprising administering a total of 6 to 8 hourly doses of the first anti-FcεRIα monoclonal antibody, wherein each of the last 3 to 4 hourly doses of the first anti-FcεRIα monoclonal antibody is co-administered with a dose of a second anti-FcεRIα monoclonal antibody.

13. The method of claim 12, wherein each subsequent dose of the second anti-FcεRIα monoclonal antibody is an equal dose compared to a first dose of the second anti-FcεRIα monoclonal antibody.

14. The method of claim 12, wherein each dose of the second anti-FcεRIα monoclonal antibody is lower than a level required to induce shock.

15. The method of claim 12, wherein each dose of the second anti-FcεRIα monoclonal antibody is the same as each dose of the first anti-FcεRIα monoclonal antibody.

16. The method of claim 12, wherein the first anti-FcεRIα monoclonal antibody is IE7, wherein IE7 comprises a heavy chain variable region comprising SEQ ID NO: 3 and a light chain variable region comprising SEQ ID NO: 4.

17. The method of claim 16, wherein the second anti-FcεRIα monoclonal antibody is IB10, wherein IB10 comprises a heavy chain variable region comprising SEQ ID NO: 1 and a light chain variable region comprising SEQ ID NO: 2.

18. The method of claim 17, wherein the first anti-FcεRIα monoclonal antibody and the second anti-FcεRIα monoclonal antibody each bind to a different epitope of human or rhesus monkey FcεRIα.

19. A monoclonal antibody that specifically binds human or rhesus monkey FcεRIα, wherein said antibody is IE7 and wherein said antibody comprises a heavy chain variable region comprising SEQ ID NO: 3 and a light chain variable region comprising SEQ ID NO: 4.

20. A monoclonal antibody that specifically binds human or rhesus monkey FcεRIα that is not IgE-associated, wherein said antibody is IB10 and wherein said antibody comprises a heavy chain variable region comprising SEQ ID NO: 1 and a light chain variable region comprising SEQ ID NO: 2.

* * * * *